United States Patent [19]
Tsuzuki et al.

[11] Patent Number: 5,925,814
[45] Date of Patent: Jul. 20, 1999

[54] ELECTROLYTIC EXHAUST SENSOR WITH DIFFUSION LAYER INHIBITING FORMATION OF A LIQUID PHASE

[75] Inventors: Masashi Tsuzuki; Takeshi Kawai, both of Aichi, Japan

[73] Assignee: NGK Spark Plug Co., Ltd., Nagoya, Japan

[21] Appl. No.: 09/019,605

[22] Filed: Feb. 6, 1998

[30] Foreign Application Priority Data

Feb. 6, 1997 [JP] Japan .................................... 9-023908

[51] Int. Cl.$^6$ .................................................. G01N 27/407
[52] U.S. Cl. ........................ 73/23.32; 204/429; 204/428
[58] Field of Search .............................. 73/31.05, 31.06, 73/23.31, 23.32; 204/424, 425, 426, 427, 428, 429

[56] References Cited

U.S. PATENT DOCUMENTS 5,700,367  12/1997  Yamada et al. ........................ 204/426
5,709,787   1/1998  Lim ........................................ 204/425
5,787,866   8/1998  Sugiyama et al. ..................... 204/426

FOREIGN PATENT DOCUMENTS

6-174683  6/1994  Japan .

*Primary Examiner*—Michael Brock
*Attorney, Agent, or Firm*—Foley & Lardner

[57] ABSTRACT

A gas sensor has a sensor cell unit which includes a detection member made up of an oxygen concentration cell, oxygen pump cell and a spacer interposed between the oxygen concentration cell and the oxygen pump cell to define therebetween a measurement gas chamber. The spacer has a pair of communicating holes for providing communication between the measurement gas chamber and the outside. Diffusion control layers made of porous material are formed within the communicating holes of the spacer so as to control flow of the detection gas into the measurement gas chamber, etc. The diffusion control layer is made of alumina and has on the outer surface thereof (i.e., on the inner peripheral surfaces thereof defining gas permeating pores) a thin Ca coating which inhibits formation of a substance which is in a liquid phase at a temperature range in which the gas sensor is used, due to reaction of the alumina forming the diffusion control layer with a suspended component of the detection gas such as phosphorus (P) in an engine exhaust gas.

10 Claims, 6 Drawing Sheets

ELECTROLYTIC EXHAUST SENSOR WITH DIFFUSION LAYER INHIBITING FORMATION OF A LIQUID PHASE

BACKGROUND OF THE INVENTION

1. Field of the Invention

The present invention relates to a gas sensor having a porous member through which gas is permeable, such as an oxygen sensor for measuring the oxygen concentration of the exhaust gases emitted from automobiles.

2. Description of the Related Art

With a view to reducing CO, NOx, HC contained in the exhaust gases emitted from automobiles, it has heretofore been practiced to dispose an oxygen sensor at an exhaust system and control an air/fuel ratio of an air/fuel mixture to be supplied to an engine on the basis of an output of the oxygen sensor.

An example of an oxygen sensor used for such air-fuel ratio control is a wide-range air/fuel ratio sensor which includes a measurement gas chamber between an oxygen concentration cell and an oxygen pump cell and a diffusion control layer between the measurement gas chamber and a surrounding measurement gas. The diffusion control layer is a porous layer through which gas penetrates or permeates and controls the diffusion of detection gas (exhaust gas) introduced from the outside into the measurement gas chamber.

In general, some fuels and engine oils for internal combustion engines such as automotive engines contain phosphorus (P), and if such fuels and engine oils containing phosphorus (P) are used, the exhaust gases having gaseous phosphorus particles are emitted from the engines. This, however, causes such a problem that the phosphorus particles (spattered or suspended component) adhere to the diffusion control layer to clog or stop up the pores through which gas penetrates.

Since the temperature of the exhaust gases to which the oxygen sensor is applied is usually considerably high so that there may occurs such a case in which when the phosphorus particles adhere to the diffusion control layer in use of the oxygen sensor the phosphorus (P) and the material constituting the diffusion control layer react to produce a substance which is in a liquid phase at the temperature in use of the oxygen sensor. By this, a glasslike substance which is a reactant of phosphorus (P) piles up on the surface of the diffusion control layer, etc. to stop up or clog the pores through which gas penetrates. Such "stopping up" or "clogging" causes a variation of the resistance to diffusion of gas, so it is no more possible to carry out accurate detection of the air/fuel ratio.

Against such a "clogging" problem, a counterplan of adjusting the porosity and the diameter of the pores of the porous material has been made but not entirely satisfactorily.

Particularly, as the regulations on the exhaust gas emission have been becoming more stringent in recent years, more accurate air/fuel ratio control is necessitated. Furthermore, the reliability over an elongated period of usage is also demanded, so much more improvement in the oxygen sensor is eagerly demanded.

SUMMARY OF THE INVENTION

According to an aspect of the present invention, there is provided a novel and improved gas sensor which includes a detection portion and a porous member forming gas permeating pores through which detection gas is introduced into the detection portion, wherein the porous member includes a material inhibiting formation of a substance which is in a liquid phase at a temperature range in which the gas sensor is used, due to reaction of the porous member with a suspended component of the detection gas. By this, the suspended component is hard to react with a material of the porous member and produce a substance in a liquid phase. By this effect, "clogging" or "stopping up" of the gas permeating pores is hard to occur, so the durability of the gas sensor is improved.

The above described inhibiting material of the porous member can be a single element or a compound, provided that it can inhibit formation of a substance in a liquid phase. In this connection, in case a simple substance is to be carried as the above described inhibiting material on a base material to constitute the porous member, an element serving as the simple substance can be carried on the base material by immersing or dipping the base material into a solution (e.g., an aqueous solution) of a salt of the element to be carried (i.e., a salt which decomposes at low temperature) or applying the solution to the base material by using a brush and thereby adhering the salt to the base material, and thereafter heat treating the base material.

Further, in case a compound is to be carried as the above described inhibiting material on some base material to constitute a porous member, the compound can be carried on the base material by immersing the base material into a solution (e.g., an aqueous solution) of the compound or by applying the solution to the base material by using a brush, and thereafter heat treating the base material. In the meantime, calcium phosphate and magnesium phosphate are suitable as the compound since they are excellent in ability to capture phosphorus (P) and are hard to be in a liquid phase even after capturing phosphorus (P).

Further, the entire of the porous member can be constituted by the material inhibiting formation of the substance in a liquid phase or the porous member can includes the inhibiting material at a predetermined rate or a portion of the porous member can be constituted by the inhibiting material.

Examples of the above described gas sensor are an oxygen sensor whose output changes abruptly in the theoretical air/fuel ratio condition and a wide-range air/fuel ratio sensor which can detect the air/fuel ratio over a wide range.

An example of the above described detection portion is a gas detection cell having a pair of electrodes (e.g., a reference electrode and a measurement electrode) provided to a substrate made of a gas sensitive ceramic material. Examples of the gas sensitive material are a solid electrolyte (e.g., zirconia) which is operable to produce a variable electromotive force in response to a variation of the oxygen concentration of the detection gas and a resistance varying type material such as titania whose internal resistance varies in response to a variation of the oxygen concentration of the detection gas.

According to another aspect of the present invention, the inhibiting material of the porous member inhibits formation of a substance in a liquid phase due to reaction of the porous member with phosphorus (P) which is the suspended component of the detection gas.

Namely, an example of the suspended component that is liable to cause "clogging" is phosphorus, so an oxygen sensor that detects the oxygen concentration of the exhaust gas can have an advantage of being hard to get clogged through selection of the inhibiting material, i.e., by selecting the inhibiting material so as to be hard to produce a substance in a liquid phase as a result of reaction with phosphorus (P).

According to a further aspect of the present invention, the porous member comprises a diffusion control layer.

If the diffusion control layer gets clogged, the degree of diffusion control is caused to vary, thus producing an undesirable influence on the output of the gas sensor. However, according to the present invention, the gas permeating pores of the diffusion control layer are hard to get clogged, so the gas sensor of this invention has a good durability and can detect, for example, the oxygen concentration and so on of the exhaust gas accurately over an elongated period of usage.

According to a further aspect of the present invention, the diffusion control layer has a larger diffusion resistance at an inner part thereof and a smaller resistance at an outer part thereof. The poisoning substance such as phosphorus (P) naturally adheres more to the detection gas-introduced side (i.e., the outer side) of the diffusion control layer, so it is inevitable that "clogging" is prone to be caused at the outer part of the porous member. According to the present invention, it is set that the diffusion resistance at the outer part is smaller (e.g., pore size is larger or roughly meshed), so even if the poisoning substance adheres a little to the outer part to cause the outer part to partly increase in the diffusion resistance the influence on the diffusion resistance of the entire diffusion control layer is small, thus making it possible for the gas sensor to produce a good output.

According to a further aspect of the present invention, the porous member comprises a porous, protective layer covering a measurement electrode of the gas sensor. While the protective layer is not provided to perform a diffusion control like the above described diffusion control layer, "clogging" of the projective layer is not desirable if it causes the detection gas to be hard to reach the electrode and exerts a bad influence on the output of the gas sensor. Thus, according to the present invention, "clogging" is hard to occur also at the protective layer, so measurement of the oxygen concentration, etc. can be attained suitably.

According to a further aspect of the present invention, the above described temperature range is equal to or larger than 500° C. In this temperature range, adherence of phosphorus (P) or the like to the diffusion control layer of the oxygen sensor is liable to cause a substance in a liquid phase. However, by using the gas sensor having a structure of the present invention in such a temperature range, accurate measurement can be attained over an elongated period of usage. In the meantime, in case the temperature is equal to or higher than 700° C., a substance in a liquid phase is more prone to be produced. However, even in such a severe condition, the gas sensor having a structure of the present invention can be used successfully.

According to a further aspect of the present invention, at least part of the porous member is made of calcium phosphate whose Ca/P ratio is 1.0 or more. When phosphorus (P) adheres to the porous member made of calcium phosphate whose Ca/P ratio is 1.0 or more, such a chemical change that the Ca/P ratio reduces gradually occurs due to reaction of phosphorus (P) with calcium phosphate. However, so long as the Ca/P ratio is equal to or larger than 1.0, a substance resulting from such reaction is not held in the solid phase but in the liquid phase over a high temperature range as shown in the equilibrium diagram of FIG. 4 which will be described hereinlater. Accordingly, in a temperature range for normal or usual use of the gas sensor, the substance resulting from the reaction is in the solid state, so the solid substance containing phosphorus (P) is not piled up so tightly and closely as the liquid phase substance, thus not causing "clogging" due to formation of a glasslike substance.

Particularly, calcium phosphate is suitable for the above described end since it is high in reactivity with phosphorus (P) and excellent in the ability to capture phosphorus (P) so that phosphorus (P) is hard to reach the electrode of the gas sensor.

According to a further aspect of the present invention, the porous member comprises a plurality of porous layers including an outermost layer which is made of calcium phosphate whose Ca/P ratio is 1.0 or more. In case the Ca/P ratio is equal to or larger than 1.0, "clogging" due to formation of a liquid-phase substance or a glasslike substance is hard to occur as described above, so by disposing a layer having such a composition at an outer side it can operative more effectively with respect to the suspended phosphorus (P) to prevent "clogging" effectively.

Further, in case the porous member comprises a diffusion control layer, the inner layer can be structured so as to serve as a layer for carrying out diffusion control while the outer layer can be structured so as to serve as a layer for preventing "clogging", i.e., each layer can be allotted to a different task or work, so each layers can be structured so as to function optimally.

According to a further aspect of the present invention, the above described inhibiting material of the porous member is Mg or Ca and in the form of a coating which is applied to an outer surface of the porous member, or the porous member is coated with Mg or Ca. The outer surface of the porous member means the surfaces of the walls defining the gas permeating pores (e.g., the inner peripheral surfaces of the pores). Mg and Ca are high in the ability to capture phosphorus (P) and does not cause a liquid-phase substance but a solid-phase substance as a result of reaction with phosphorus (P), thus making it possible to prevent "clogging" due to formation of a glasslike substance as in the prior art. Particularly, it is more desirable to apply a coating of Mg or Ca to the outer surface of the porous member which is made of calcium phosphate whose Ca/P ratio is equal to or larger than 1.0 since a pronounced effect can be attained.

DETAILED DESCRIPTION OF THE PREFERRED EMBODIMENTS

A preferred embodiment of a gas sensor will be described in detail hereinlater.

(First Embodiment)

A gas sensor of this embodiment is an oxygen sensor to be attached to, for example, an automotive exhaust system for measuring an oxygen concentration (i.e., air/fuel ratio) of a detection gas (i.e., exhaust gas), particularly a wide-range air/fuel ratio sensor capable of detecting an air/fuel ratio over a wide range.

a) The oxygen sensor of this embodiment consists of a sensor cell unit in the form of sheet or plate, chiefly made of ceramic and disposed within a metallic tubular receptacle (not shown).

Figure 1:
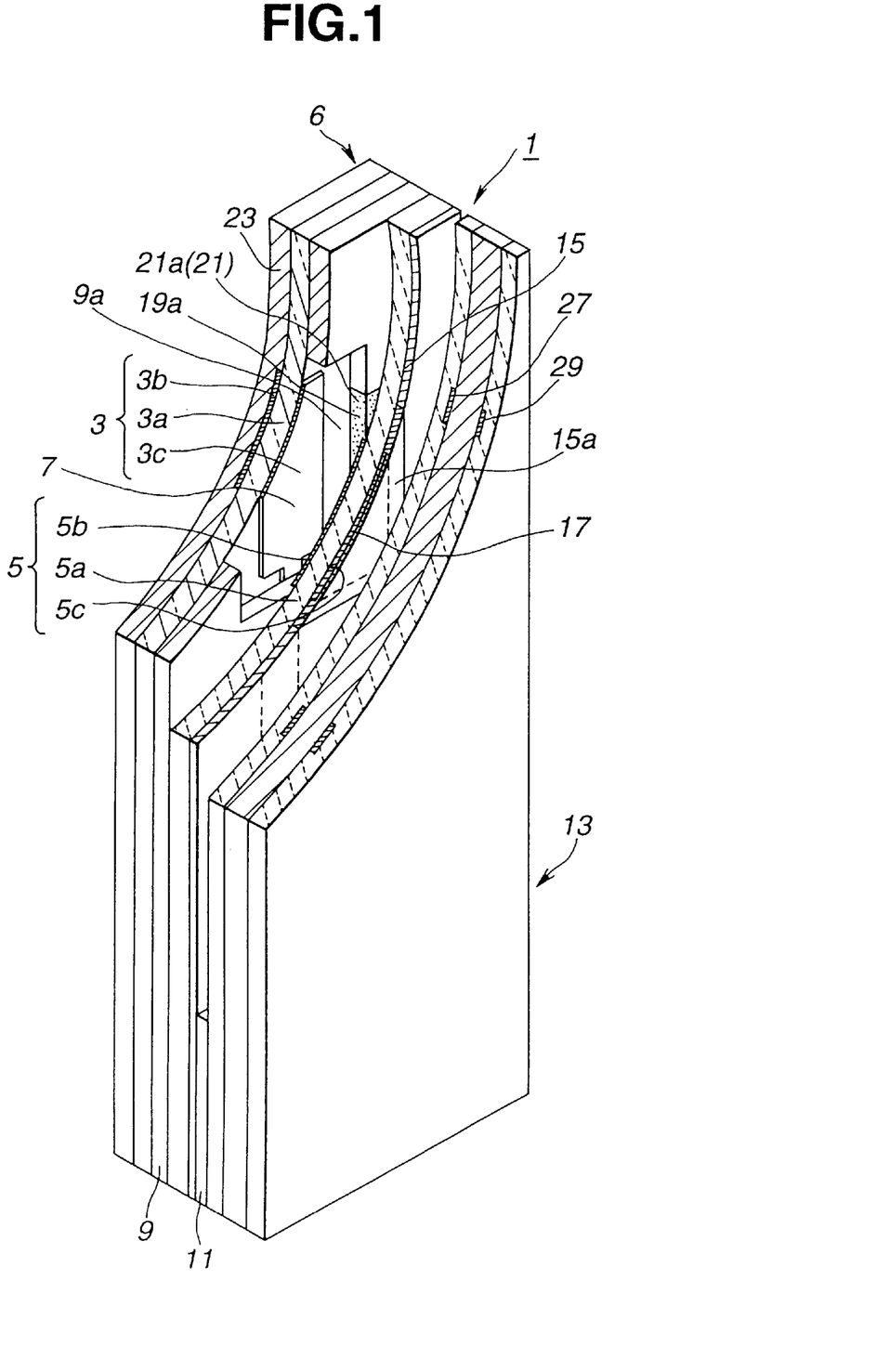
FIG. 1 is a perspective, partly exploded view of an oxygen sensor according to a first embodiment of the present invention.
Figure 2:
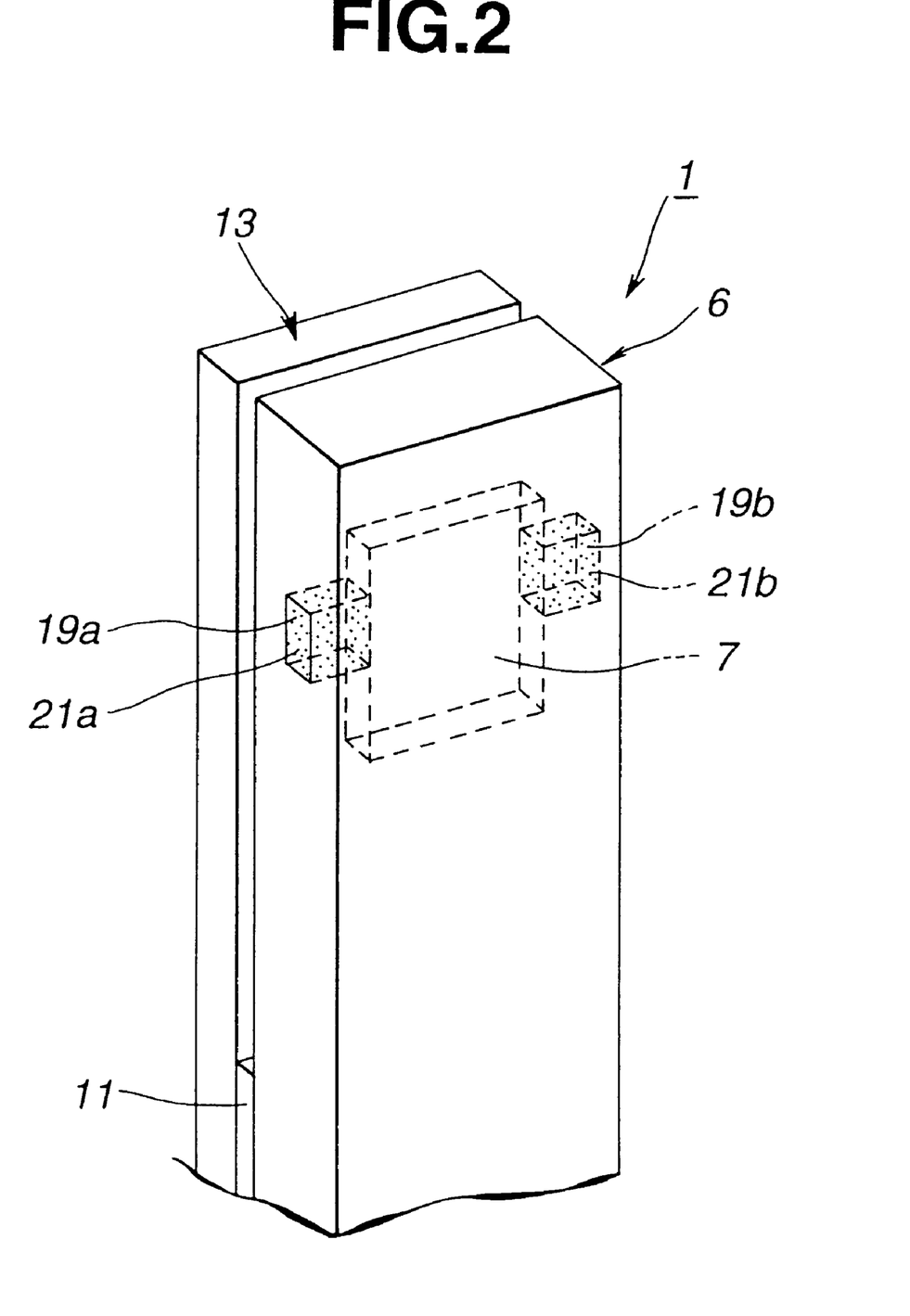
FIG. 2 is a fragmentary perspective view of the oxygen sensor of FIG. 1 for illustration of diffusion control layers of a sensor cell unit thereof.

As shown in FIGS. 1 and 2, the sensor cell unit is generally indicated by 1 and includes a detection member 6 which is constituted by an oxygen concentration cell 3 made up of a solid electrolytic substrate 3a and a pair of porous electrodes 3b and 3c disposed on the opposite sides of the substrate 3a, an oxygen pump cell 5 made up of a solid electrolytic substrate 5a and a pair of porous electrodes 5b and 5c disposed on the opposite sides of the substrate 5a, and a spacer 9 interposed between the above cells 3 and 5 to from a measurement gas chamber 7. The sensor cell unit 1 further includes a heater 13 disposed outside of the detection member 6 and on the oxygen pump cell 5 side of same in a way as to provide a predetermined gap between the heater 13 and the detection member 6 by means of a spacer 11 interposed therebetween.

In this instance, the both cells 3 and 5 include the solid electrolytic substrates 3a and 5a made of yttrium-zirconia solid solution and the rectangular porous electrodes 3b–3c and 5b–5c disposed on the opposite sides of the substrates 3a and 5a, respectively. The porous electrodes 3b–3c and 5b–5c are made of a common matrix of yttrium-zirconia solid solution and a remainder of platinum (Pt). In the meantime, as the material of the solid electrolytic substrate 3a and 5a, there can be used a calcium-zirconia solid solution, various solid solutions of cerium dioxide, thorium dioxide and hafnium dioxide, a Perovskite solid solution, a trivalent metallic oxide solid solution, etc. other than an yttrium-zirconia solid solution.

Further, the outer side surface of the oxygen pump cell 5 is covered by an insulation layer 15 having a hollow portion 15a corresponding in position to the porous electrode 5c. Provided to the hollow portion 15a is a porous, electrode protecting layer 17 chiefly made of alumina and covering the porous electrode 5c for protection thereof from the outside.

The above described measurement chamber 7 is formed by interposing the spacer 9 between the oxygen concentration cell 3 and the oxygen pump cell 5 and joining them together. The spacer 9 is chiefly made of alumina and has a hollow portion 9a corresponding in position to the porous electrodes 3c and 5b. To the measurement chamber 7 constituted by the hollow portion 9a, there are exposed the above described porous electrodes 3c and 5b.

The above described spacer 9 has a pair of openings 19a and 19b provided on the opposite sides of the measurement chamber 7 for communication between the measurement chamber 7 and the outside(i.e., an atmosphere surrounding the sensor cell unit 1). A porous material is filled in the openings 19a and 19b to form thereat diffusion control layers 21a and 21b. The diffusion control layers 21a and 21b control flow of the detection gas into the measurement gas chamber 7 and the like flow of same.

Particularly, the diffusion control layers 21a and 21b in this embodiment are made of alumina and formed with a thin Ca coating (not shown) on the outer surface thereof (i.e., on the inner peripheral surfaces, etc. of the gas permeating pores). In the meantime, the Ca coating may be replaced by a Mg coating or both of the Ca coating and Mg coating may be applied.

Further, adhered to the outside surface of the oxygen concentration cell 3 is a cover 23 made of solid electrolyte and covering the porous electrode 3b so that oxygen pumped up to the porous electrode 3b side when a detection circuit 25 (refer to FIG. 3) which will be described hereinlater causes very small current iCP to flow from the porous electrode 3b side of the oxygen concentration cell 3 to the porous electrode 3c side is not discharged directly therefrom. Further, the oxygen concentration cell 3 is provided with a leakage-inducing resistance portion 3d (refer to FIG. 3) for causing part of the oxygen conducted to the porous electrode 3b side in the above described manner to leak to the measurement gas chamber 7.

In the meantime, the above described heater 13 has on one side thereof, i.e., on the oxygen pump cell 5 side a heat generating pattern 27 and on the other side a known migration preventing pattern 29.

b) Referring to FIG. 3, the oxygen sensor will be described further with respect to its electric circuit and control.

Figure 3:
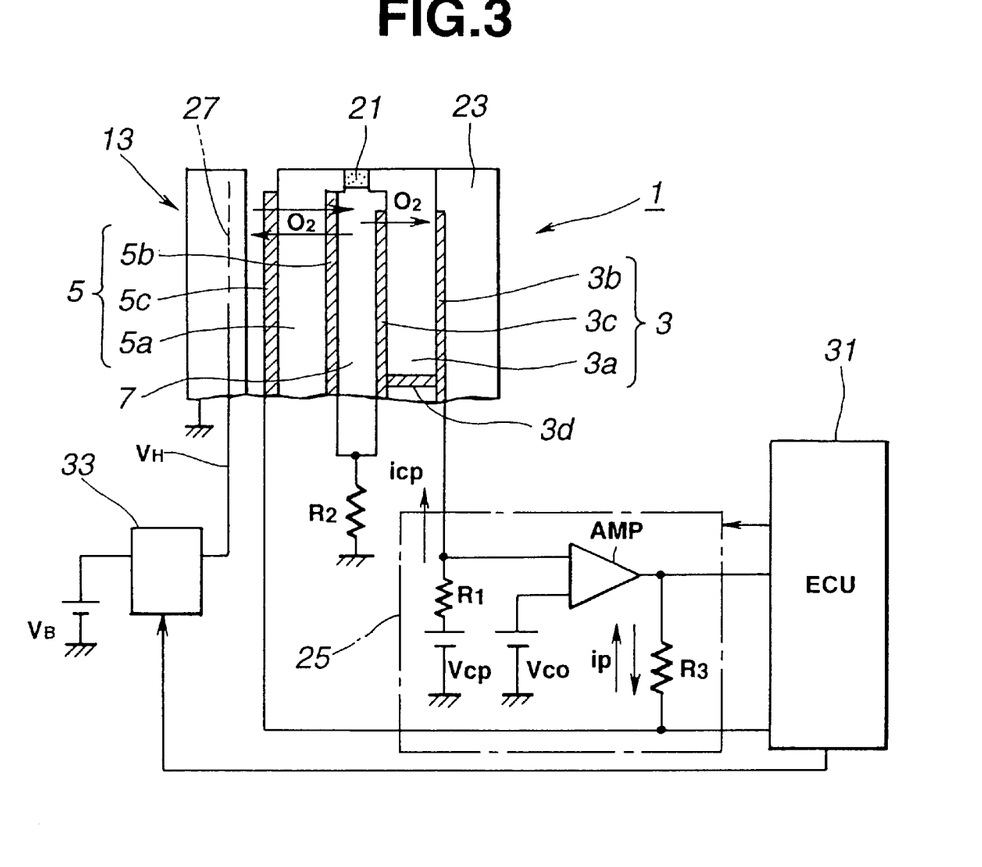
FIG. 3 is an illustration of an electrical structure of the oxygen sensor of FIG. 1.

As shown in FIG. 3, the porous electrodes 3c of the oxygen concentration cell 3 and the porous electrode 5b of the oxygen pump cell 5 adjoining the measurement gas chamber 7 are grounded by way of a resistor R2. The other porous electrodes 3b and 5c are connected to the detection circuit 25. To an end of a resistor R1 in the detection circuit 25 is connected the cover 23 side porous electrode 3b of the oxygen concentration cell 3. To the other end of the resistor R1 is applied a voltage Vcp. The resistor R1 is provided for supplying constant, very small current iCP to the oxygen concentration cell 3 and its resistance is set so as to be sufficiently larger as compared with that of a resistor R2 and an internal resistance of the oxygen concentration cell 3.

Further, the porous electrode 3b of the resistor R1 is connected to a minus side input terminal of a differential amplifier AMP. To the plus side input terminal of the differential amplifier Amp is applied a reference voltage Vco, so that a voltage proportional to the difference between the reference voltage Vco and the voltage across the porous electrode 3b side of the oxygen concentration cell 3 is outputted. Further, the output terminal of the differential amplifier AMF is connected through a resistor R3 to the heater 13 side porous electrode 5c of the oxygen pump cell 5. As a result, a pump current ip can flow through the oxygen pump cell 5 in opposite directions in response to an output of the differential amplifier AMF.

The detection circuit 25 is constructed to control the oxygen concentration within the measurement chamber 7 in a way as to maintain it constant by allowing a small current iCP to flow through the oxygen concentration cell 3 and thereby pumping oxygen up to the porous electrode 3b such that the porous electrode 3b functions as an internal reference oxygen source and a voltage proportional to the oxygen concentration within the measurement gas chamber 7 is produced across the opposite ends of the oxygen concentration cell 3, and further by making a pump current ip be supplied from the differential amplifier AMF to the oxygen pump cell 5 so that the above described voltage (more specifically, the voltage across the opposite ends of the resistor R2) becomes equal to the reference voltage VCO.

Since the pump current iCP produced by such a control is proportional to the oxygen concentration of the surrounding measurement gas, the pump current iCP is converted to a voltage signal by means of the resistor R3 and the converted voltage signal is outputted as a detection signal representative of the oxygen concentration of the exhaust gas and therefore the air/fuel ratio to an electronic control circuit (hereinafter referred to as ECU) made up of a microcomputer, etc. for a control of an internal combustion engine.

To the heat generation pattern 27 of the heater 13 is applied a heater voltage VH by way of a voltage changing circuit 33. The voltage changing circuit 33 is constructed so as to be capable of outputting, for example, a battery voltage VB and its alterations or variations as the heater voltage VH to be applied to the heater 13 and apply either of such various voltages to the heat generation pattern 27 as the heater voltage VH in response to a voltage changing command outputted from the ECU 31.

c) The method of making the sensor cell unit 1 of the oxygen sensor having the above described structure will be described briefly.

Firstly, yttrium-zirconia powder mixed with PVB binder and organic solvent is used to prepare by means of the known doctor blade technology green sheets from which the solid electrolytic substrate 3a of the oxygen concentration cell 5 and the solid electrolytic substrate 5a of the oxygen pump cell 5 are to be formed respectively.

Then, a material consisting of platinum and yttrium-zirconia matrix is mixed with a PVB binder and organic solvent and formed into a paste, and then the thus prepared paste is printed on the respective green sheets described as above to form electrode patterns from which the porous electrode 3b and 3c on the solid electrolytic substrate 3a and the porous electrodes 5b and 5c on the solid electrolytic substrate 5a are to be formed respectively.

The thus prepared green sheets with the printed patterns and green sheets for the insulation layer 15, cover 23, spacer 9, etc. which are prepared in the similar manner are placed one upon another and adhered or joined together by pressure.

In this instance, the green sheet for the spacer 9 is formed with the hollow portion 9a and the communicating holes 19a and 19b. In this embodiment, the green sheet for the space 9 is first adhered to the other green sheets by pressure and then a paste for forming the diffusion control layers 21a and 21b is filled in the openings for the communicating holes 19a and 19b by printing. The paste is made of alumina powder mixed with PVB binder and organic solvent and formed into a porous layer having a number of gas permeating pores when sintered.

The above described green sheets, etc. having been placed one upon another and adhered by pressure are sintered at the temperature of 1500° C., whereby to obtain the detection member 6.

Thereafter, the diffusion control layer 21 is coated with Ca. In this instance, an aqueous solution of calcium acetate of the concentration of 24% by weight for instance is applied dropwise to the diffusion control layer 21 by the amount of 0.1 $\mu$l and sintered at 1250° C. for thirty minutes. By this, the surface of the alumina mass constituting the diffusion control layer 21 (i.e., the inner peripheral surfaces of the gas permeating pores) is coated with Ca. The aqueous solution of calcium acetate infiltrate into the diffusion control layer 21 while wetting the inner peripheral surfaces of the gas permeating pores, so the Ca coating is formed through the diffusion control layer 21.

On the other hand, the heater 13 is produced by printing a mass of paste for the heat generation pattern 27 on a green sheet made of alumina, placing this and other green sheets one upon another, and sintering them similarly to the detection member 6.

The sintered detection member 6 and heater 13 are adhered by means of a heat-resisting inorganic adhesive to constitute the sensor cell unit 1. Apart from this, the green sheet, etc. for the detection member 6 and the green sheet, etc. for the heater 13 may be placed one upon another and sintered at the same time to constitute the sensor cell unit 1.

The oxygen sensor produced in the above described manner according to the present invention has the Ca coating which is formed on the entire surfaces of the gas permeating pores of the diffusion control layer 21, so it becomes possible to prevent the component (alumina) of the diffusion control layer 21 from reacting with phosphorus (P) and forming a liquid-phase substance even when the phosphorus (P) in the exhaust gases adheres to the diffusion control layer 21, as will be apparent from the result of experiments which will be described hereinlater.

In this embodiment, the phosphorus (P) adhering to the surfaces of the gas permeating pores reacts with the calcium (Ca) disposed on the surfaces of the gas permeating pores to form phosphoric acid, so a phosphoric compound in a liquid phase is never formed as in the prior art and therefore it never occurs that a phosphoric compound in a glassy state is formed to clog or stop up the gas permeating pores. For this reason, the oxygen sensor of this embodiment has such an advantage of being hard to vary in the diffusion resistance and being durable over an elongated period of usage.

In the meantime, for applying a Mg coating to the surfaces of the gas permeating pores in place of calcium (Ca) or additionally on the Ca coating, an aqueous solution of magnesium acetate is used. By the provision of such a Mg coating, the phosphorus (P) adhering to the surface of the diffusion control layer 21 does not form a liquid-phase phosphoric compound but a solid-phase phosphoric magnesium, thus not causing "clogging" of the gas permeating pores.

(Second Embodiment)

This embodiment is substantially similar to the first embodiment except for the diffusion control layer, so description will be made only to the different point.

The diffusion control layer of this embodiment contains calcium phosphate of the Ca/P rate of 1.0 or more (e.g., 1.67). The diffusion control layer is made of a composite material of about 80% by weight of $Ca_{10}(PO_4)_6(OH)_2$ and about 20% by weight of $Ca_3(PO_4)_2$.

For making such a diffusion control layer, a green sheet for a spacer having hollow portions for the communicating holes is placed on another green sheet. Then, in the hollow potions is filled by printing a paste which will become phosphoric calcium after sintering.

The paste contains $Ca_{10}(PO_4)_6(OH)_2$ and is produced in the following manner.

Powder of apatite hydroxide is provisionally baked at 1200° C., added with an ethyl cellulose binder containing 20% by weight of solid matter, butyl carbitol containing 60% by weight of solid matter, and sublimation resin filler for forming of pores, containing 13% by weight of solid matter, and mixed to from paste by using a mixing machine.

Thereafter, the above described green sheet for the spacer is placed on other green sheets and joined together by pressure and then sintered at 1500° C. for about two hours, whereby to complete the detection member.

As described above, the diffusion control layer in this embodiment is made of calcium phosphate of the Ca/P rate of 1.0 or more, so similarly to the first embodiment the phosphorus (P) adhering to the surfaces of the gas permeating pores reacts with Ca of the calcium phosphate whose Ca/P ratio is 1.0 or more and which constitutes the surfaces of the walls defining the gas permeating pores to form solid-phase calcium phosphate and not form a liquid-phase substance, thus not causing "clogging" of the gas permeating pores.

The reason why will be described with reference to the phase diagram of $CaO-P_2O_5$ in FIG. 4.

Figure 4:
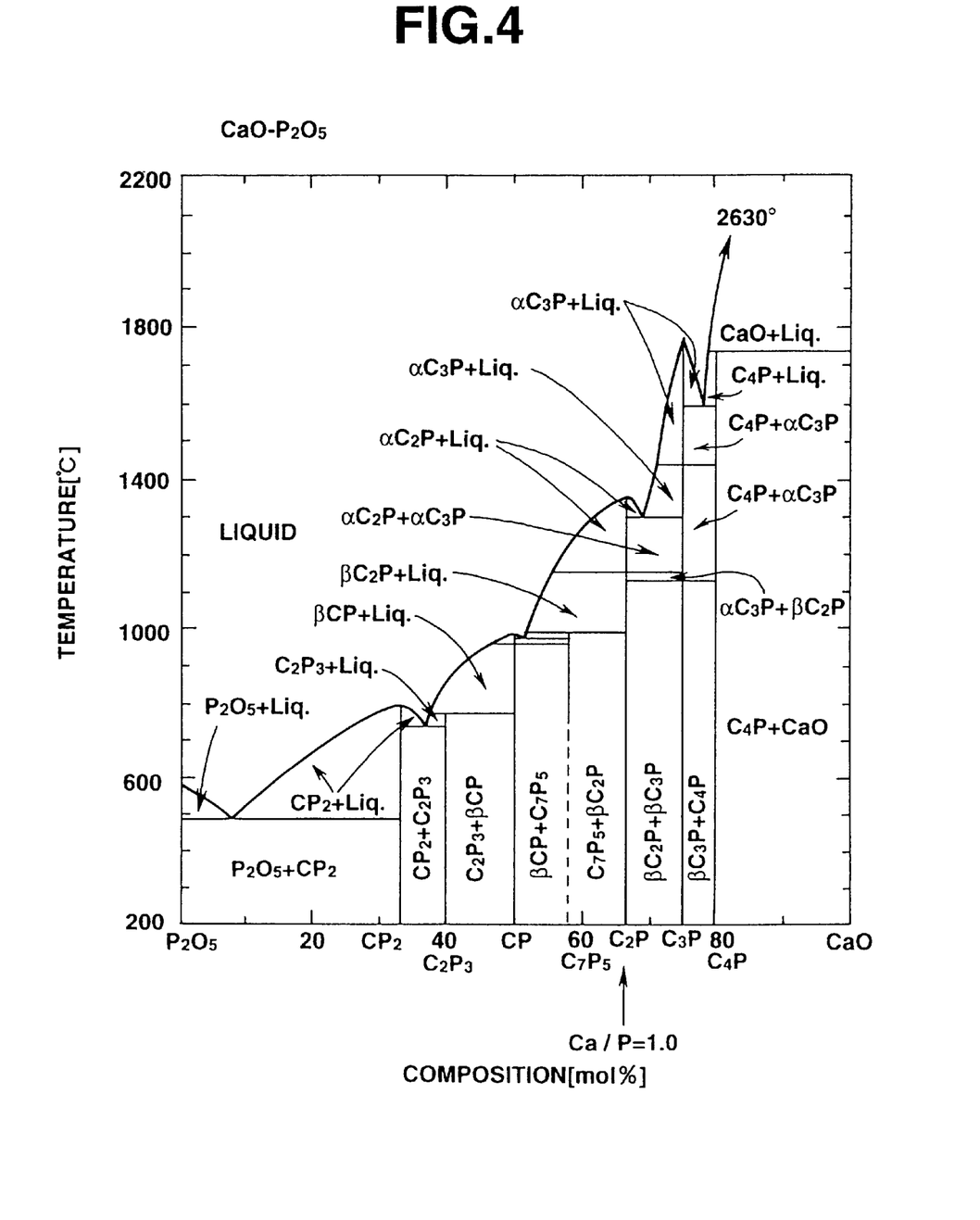
FIG. 4 is a phase diagram of a material constituting a diffusion control layer for an oxygen sensor according to a second embodiment of the present invention.

In the area where the Ca/P ratio is 1.0 or more, i.e., in the area on the right-hand side of the $C_2P$ equilibrium in FIG. 4, the solid state is maintained even when the temperature rises to a considerably high value. Further, in the area on the left-hand side of the $C_2P$ equilibrium in the same figure, a liquid phase is liable to be caused. Accordingly, when calcium phosphate of the Ca/P rate of 1.0 or more is used, a liquid phase is hardly caused at once even if the phosphorus (P) in the exhaust gases adheres to the diffusion control layer to decrease the Ca/P ratio gradually, so it will be understood that "clogging" is hard to be caused.

In the meantime, while it has been described that calcium phosphate of the Ca/P ratio of 1.0 or more is used in this embodiment for the diffusion control layer, a Mg or Ca coating may further be formed on the surfaces of the pores of the diffusion control layer similarly to the first embodiment.

(Third Embodiment)

This embodiment mainly differs in the diffusion control layer from the first embodiment, so that only the different point will be described.

Figure 5:
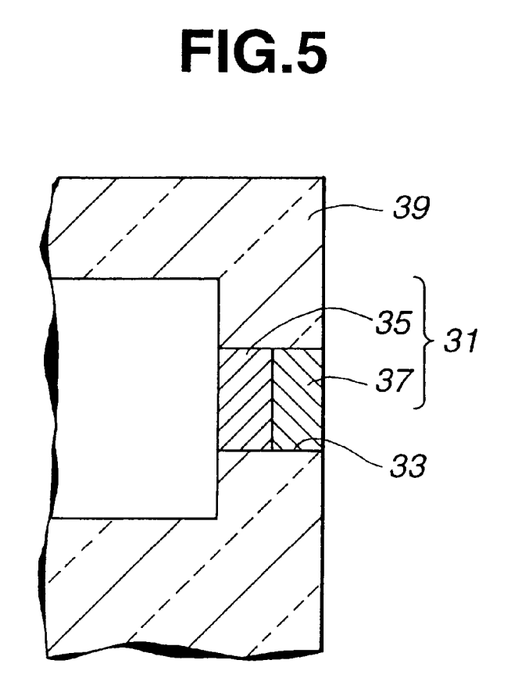
FIG. 5 is a fragmentary sectional view of a sensor cell of an oxygen sensor according to a third embodiment of the present invention.

As shown in FIG. 5, the diffusion control layer 31 in this embodiment has a two-layered structure and includes an outer layer section 35 and an inner layer section 37 which are disposed side by aside within the communicating hole 33.

The inner one 35 of those layer sections is made of similar alumina to the conventional and provided mainly for diffusion restriction (i.e., has a larger diffusion resistance). On the other hand, the outer layer section 37 is provided for removal of deposit of phosphorus (P) and so on (i.e., has a smaller diffusion resistance) and made of a composite material of calcium phosphate which is of the Ca/P ratio of 1.63. The outer layer section 37 is made of a composite material containing calcium phosphate of the Ca/P ratio of 1.0 or more (e.g., 1.63), i.e., a composite material containing about 80% by weight of $Ca_{10}(PO_4)_6(OH)_2$ and about 20% by weight of $Ca_3(PO_4)_2$.

For forming the above described diffusion control layer 31, the green sheet for the spacer 39, having hollow portions for the communicating holes 33 is placed upon another green sheet. Then, a mass of paste of the material for forming the inner layer section 35 and a mass of paste of the material for forming the outer layer section are applied to the hollow portions by printing. Thereafter, similarly to the first embodiment, the green sheet for the spacer 39 and other green sheets are placed one upon another and sintered.

Since in this embodiment the diffusion control layer 31 is two-layered and includes the inner layer section 35 for actually restricting diffusion and the outer layer section 37 for removing deposition of phosphorus (P) and so on, thus enabling the diffusion layer 31 to have such a structure that makes the best use of the respective functions.

Namely, for the inner layer section 35 it becomes possible to use, for example, alumina or the like that is excellent in the workability and the strength, etc. and assuredly form the gas permeating pores for restriction of diffusion, on the other hand for the outer layer section 37 it becomes possible to attain an optimum composition which allows phosphorus (P) to adhere thereto and form a compound in a solid state, thus making it possible to utilize the respective functions sufficiently.

(Fourth Embodiment)

This embodiment mainly differs in the diffusion control layer from the first embodiment, so that only the different point will be described.

Figure 6:
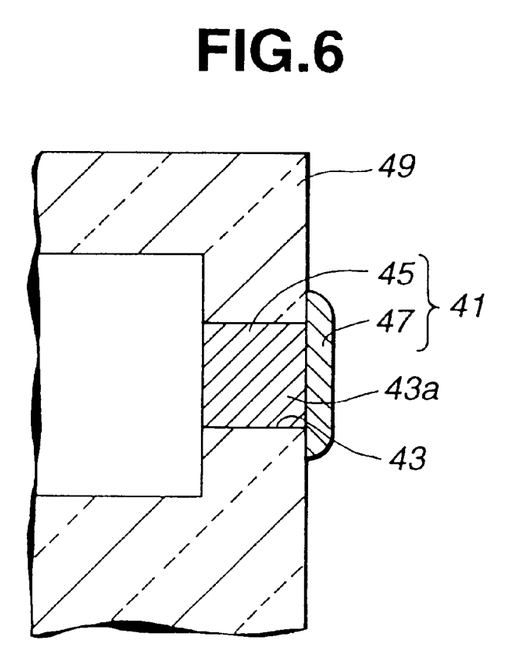
FIG. 6 is a view similar to FIG. 5 but shows a fourth embodiment of the present invention.

As shown in FIG. 6, the diffusion control layer 41 in this embodiment has a two-layered structure and includes an inner layer section 45 disposed within the communicating hole 43 and an outer layer section 47 covering the outer opening end 43a.

The inner one 45 of those layer sections is made of alumina and restricts diffusion similarly to that in the third embodiment. On the other hand, the outer layer section 47 is provided to remove deposition of phosphorus (P) and so on and is made of the similar material to that in the second embodiment, i.e., made of a composite material containing calcium phosphate of the Ca/P ratio of 1.0 or more (e.g., 1.63), i.e., a composite material containing about 80% by weight of $Ca_{10}(PO_4)_6(OH)_2$ and about 20% by weight of $Ca_3(PO_4)_2$.

For forming the diffusion control layer 41 of such a two-layered structure, the green sheet for the spacer 49, having a hollow portion for the communicating opening 43 is placed on another green sheet. A mass of paste of the material for forming the inner layer section 45 is applied to the hollow portion by printing. Thereafter, similarly to the first embodiment, the above described green sheet and other green sheets are placed one upon another. A mass of paste of the material for the outer layer section 47 is applied by printing to the outer opening end 43a so as to cover the outside of the inner layer section 45 and thereafter sintered.

As described above, similarly to the third embodiment, the diffusion control layer 41 in this embodiment is two-layered and includes the outer layer section 47 for actually restricting diffusion and the outer layer section for removing deposition of phosphorus (P) and so on, thus making it possible to utilize the respective functions sufficiently.

Particularly, since in this embodiment the outer layer section 47 is formed on the side surface of the detection member, there results an advantage that the diffusion layer 41 can have an enlarged effective area for removal of the deposition.

While this embodiment has been described as that the inner layer section 45 and the outer layer section 47 are sintered simultaneously, the inner layer section 45 may be once sintered together with the green sheet for the spacer 49, then the work for adjustment of the sintered inner layer section 45 with respect to its diffusion control is made, thereafter a mass of paste for the outer layer section 46 is applied to the side surface of the detection member, and sintering may be carried out once again.

(Experiment)

Experiments having been made by using oxygen sensors of the above described embodiments will be described.

The experiments are a phosphorus (P) poisoning durability test and were made for investigating a variation of diffusion resistance due to "clogging" or "stopping up" caused by adherence of phosphorus (P).

More specifically, the oxygen sensor of each of the above described embodiments and an comparative example of a prior art oxygen sensor were installed on an engine exhaust pipe, and the deteriorated condition (i.e., clogged condition) of the diffusion control layer was investigated based on a change of a change rate of ip current ($\Delta$ip) with the passage of time. The result of the experiments is shown in table 1, table 2 and FIG. 7.

Experimental conditions;

engine; 2-litter in-line 4-cylinder gasoline engine, N.A. (Normal Aspiration)

set air/fuel ratio; $\lambda=1$ driving condition; driving with no applied load and at constant speed of 3000 rpm fuel; regular gasoline+Zn-DBP (applied amount: 50 cc/2 litters)

heat treatment temperature of coating (i.e., layer for removal of deposition); example No. is 1000° C., and example No. 11 is 500° C.

TABLE 1

| Sample No. | Layer for diffusion Control | Layer for Removal of Deposit | Ca/P Ratio | Coating | Remarks (Laminar Structure) |
|---|---|---|---|---|---|
| Invention | | | | | |
| 1 | Alumina | — | — | Ca | the same with 1st Embodiment |
| 2 | Alumina | — | — | Mg | the same with 1st Embodiment |
| 3 | $Ca_{10}(PO_4)_6 \cdot (OH)_2$ | $Ca_{10}(PO_4)_6 \cdot (OH)_2$ | 1.67 | Al | the same with 2nd Embodiment |
| 4 | $Ca_{10}(PO_4)_6 \cdot (OH)_2$ | $Ca_{10}(PO_4)_6 \cdot (OH)_2$ | 1.67 | Ca | the same with 2nd Embodiment |
| 5 | Alumina | $Ca_{10}(PO_4)_6 \cdot (OH)_2 + Ca_3(PO4)_2$ | 1.63 | — | the same with 3rd Embodiment |
| 6 | Alumina | $Ca_{10}(PO_4)_6 \cdot (OH)_2 + Ca_3(PO4)_2$ | 1.63 | Ca | the same with 3rd Embodiment |
| 7 | Alumina | $Ca_{10}(PO_4)_6 \cdot (OH)_2 + Ca_3(PO4)_2$ | 1.63 | Mg | the same with 3rd Embodiment |
| 8 | Alumina | $Ca_{10}(PO_4)_6 \cdot (OH)_2 + Ca_3(PO4)_2$ | 1.63 | — | the same with 4th Embodiment |
| 9 | Alumina | $Ca_{10}(PO_4)_6 \cdot (OH)_2 + Ca_3(PO4)_2$ | 1.63 | Ca | the same with 4th Embodiment |
| 10 | Alumina | $Ca_2P_2O_7$ | 1.0 | — | the same with 4th Embodiment |
| Comparative Examples | | | | | |
| 11 | Alumina | — | — | Al | the same with 1st Embodiment |
| 12 | Alumina | $Ca(PO_3)_2$ | 0.5 | — | the same with 4th Embodiment |

The Ca/P ratio in table 1 is the ratio prior to coating of Ca, etc.

TABLE 2

| | $\Delta$ip[%] | | | | | |
|---|---|---|---|---|---|---|
| Sample No. | 2 hours later | 4 hours later | 6 hours later | 8 hours later | 10 hours later | 12 hours later |
| Invention | | | | | | |
| 1 | −1.8 | −30.0 | — | — | — | — |
| 2 | −3.5 | −32.0 | — | — | — | — |
| 3 | — | — | −22.8 | — | — | −78.4 |
| 4 | — | — | −7.5 | — | — | −51.1 |
| 5 | — | −1.9 | — | −8.9 | — | −30.2 |
| 6 | — | — | −3.6 | — | — | −15.1 |
| 7 | — | −1.4 | — | −3.8 | — | −8.1 |
| 8 | — | −5.5 | — | −35.0 | — | — |
| 9 | — | −2.0 | — | −10.4 | — | −27.6 |
| 10 | — | −20.0 | −25.2 | −48.7 | — | — |

TABLE 2-continued

| | $\Delta$ip[%] | | | | | |
|---|---|---|---|---|---|---|
| Sample No. | 2 hours later | 4 hours later | 6 hours later | 8 hours later | 10 hours later | 12 hours later |
| Comparative Examples | | | | | | |
| 11 | −10.7 | −44.7 | −94.3 | — | — | — |
| 12 | immeasurable at and after 2 hours | | | | | |

Figure 7:
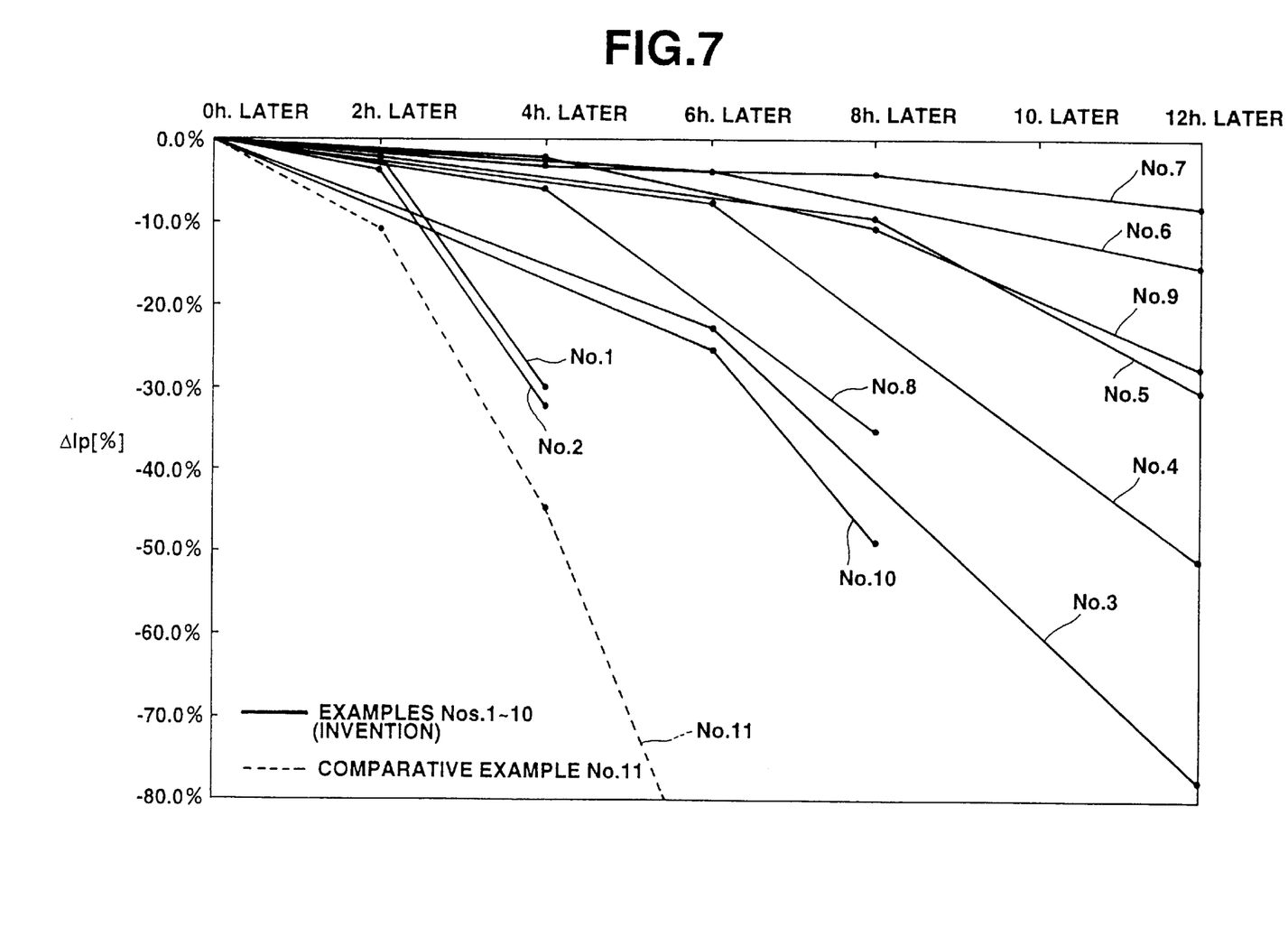
FIG. 7 is a graph of a rated variation ($\Delta ip$) of ip current as function of time.

As will be apparent from Table 1, table 2 and FIG. 7, a variation of the ip current in the oxygen sensor of each of the above described embodiments is small even after lapse of a long period of time, so the oxygen sensors of the above described embodiment can be judged as being hard to get clogged and thus excellent in durability and desirable.

In contrast to this, the comparative example of No. 11 causes a large variation of the ip current within a short period of time, so it is liable to get clogged and poor in durability and thus not desirable. Particularly, in case of the comparative example No. 12, its output reduces so as to become immeasurable after lapse of time of two hours or more, so is not desirable.

Further, as also shown in the above described test examples, a large effect can be obtained when the Ca/P ratio is equal to or larger than 1.0. However, by using calcium phosphate of the Ca/P ratio of 2.0 or more (e.g., $Ca_4P_2O_9$ can be enumerated as an example of such a substance having the Ca/P ratio of 2.0), a further large effect can be attained.

The present invention is not limited to the above described embodiments but various modifications and variations thereof can be made within the scope of the appended claims.

(1) For example, while a wide range air/fuel ratio sensor has been described and shown as an oxygen sensor embodying the present invention, the present invention may otherwise be applied to a λ sensor. For example, a protective layer covering a detection gas side of a λ sensor may be constituted by a material operable to restrict formation of the above described substance in a liquid phase.

Figure 8:
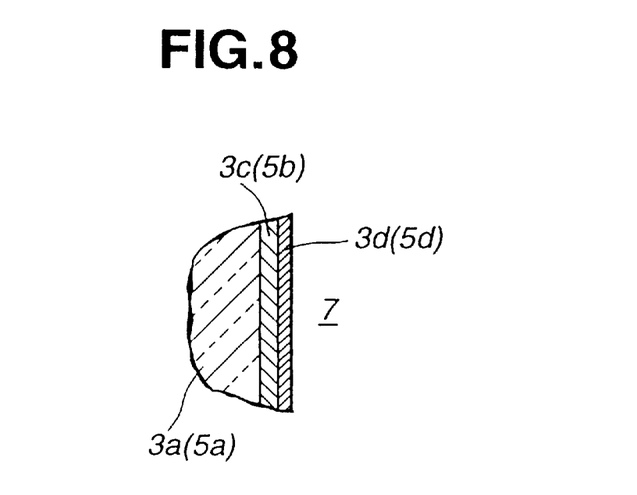
FIG. 8 is a fragmentary sectional view of a variant of the sensor cell unit of the oxygen sensor of FIG. 1.

(2) While in the above described embodiments it has been described and shown that the diffusion control layer is constructed so as to be prevented from getting clogged, this is not for the purpose of limitation, For example, as shown in FIG. 8, a protective layer 3d or 5d may be provided to the surface of an electrode (measurement electrode)3c or 5b which is exposed to detection gas, for protection of same. In this instance, the protective layer 3d or 5d may be constructed so as to be prevented from getting clogged similarly to the above described diffusion control layer.

(3) While each embodiment has been described and shown by way of example as having a coating of a single element such as Ca which is provided to an alumina substrate, a coating of a compound of calcium phosphate, magnesium phosphate or the like may be provided in lieu thereof.

What is claimed is:

1. A gas sensor including a detection portion and a porous member having gas permeating pores through which detection gas is introduced into said detection portion, wherein said porous member includes a material inhibiting formation of a substance which is in a liquid phase at a temperature range in which the gas sensor is used, due to reaction of said porous member with a suspended component of the detection gas.

2. A gas sensor according to claim 1, wherein said suspended component is phosphorus (P).

3. A gas sensor according to claim 1, wherein said porous member comprises a diffusion control layer.

4. A gas sensor according to claim 3, wherein said diffusion control layer has a larger diffusion resistance at an inner part thereof and a smaller resistance at an outer part thereof.

5. A gas sensor according to claim 1, wherein said porous member comprises a porous, protective layer covering a measurement electrode of the gas sensor.

6. A gas sensor according to claim 1, wherein said temperature range is equal to or larger than 500° C.

7. A gas sensor according to claim 1, wherein at least part of said porous member is made of calcium phosphate whose Ca/P ratio is 1.0 or more.

8. A gas sensor according to claim 1, wherein said porous member comprises a plurality of porous layers including an outermost layer which is made of calcium phosphate whose Ca/P ratio is 1.0 or more.

9. A gas sensor according to claim 1, wherein said material of said porous member is Mg or Ca and in the form of a coating applied to an outer surface of said porous member.

10. A gas sensor according to claim 1, wherein said porous member is coated with Mg or Ca.

\* \* \* \* \*